United States Patent [19]  
Nicolson

[11] Patent Number: 4,504,586  
[45] Date of Patent: Mar. 12, 1985

[54] HYBRIDOMA TUMOR CELL LINES AND THEIR MONOCLONAL ANTIBODIES TO HUMAN COLONY STIMULATING FACTOR SUBCLASS NUMBER 1

[75] Inventor: Margery Nicolson, Pacific Palisades, Calif.

[73] Assignee: Amgen, Thousand Oaks, Calif.

[21] Appl. No.: 463,516

[22] Filed: Feb. 3, 1983

[51] Int. Cl.$^3$ .................... G01N 33/54; G01N 33/56; C12N 5/00; C12N 15/00
[52] U.S. Cl. .................................... 436/518; 436/542; 436/548; 435/68; 435/240; 935/103; 935/108; 935/110; 260/112 R
[58] Field of Search ................. 435/68, 120, 240, 241; 436/548, 542, 518; 935/103, 106, 108, 110; 260/112 R

[56] References Cited

U.S. PATENT DOCUMENTS 4,172,124 10/1979 Koprowski et al. ................... 424/85
4,196,265 4/1980 Koprowski et al. ..................... 435/2

OTHER PUBLICATIONS

Baron, M. H. et al., *Cell*, 28, 395–404, (1982).
Chisholm, R. *High Technology*, 3, pp. 57–63, (1983).
Das, S. K. et al., *Blood*, 58, 630–641, (1981).
Das, S. K. et al., *J. Biol. Chem.*, 257, 13679–13684, (1982).
Das, S. K. et al., *J. Cellular Physiol.*, 104, 359–366, (1980).
Dressman, G. R. et al., *Nature*, 295, 158–160, (1982).
Engvall, E. et al., *J. Immunology*, 109, 129–135, (1972).
Goding, J. W., *J. Imm. Methods*, 39, 285–308, (1980).
Green, N. et al., *Cell*, 28, 477–487, (1982).
Hopp, T. P. et al., *P.N.A.S. (U.S.A.)*, 78, 3824–3828, (1981).
Kenneth, et al., (eds.), *Monoclonal Antibodies, Hybridomas: A New Dimension in Biological Analysis*, p. 403, New York: Plenum Press (1981), McKearn, T. J.
Kessler, S. W., *Methods in Enzymology*, 73, 422–458, (1981).
Lerner, R. A. et al., *Cell*, 23, 309–310, (1981).
Lerner, R. A. et al., *P.N.A.S. (U.S.A.)*, 78, 3403–3407, (1981).
Lerner, R. A. *Scientific American*, 248, No. 2, 66–74, (1983).
Nigg, E. A. et al., *P.N.A.S. (U.S.A.)*, 79, 5322–5326, (1982).
Oi, V. T. and L. A. Herzenberg, "Immunoglobulin Producing Hybrid", Mishell, B. B. and S. M. Shiigi (eds.), *Selected Methods in Cellular Immunology*, San Fransciso: W. H. Freeman Publishing, 1979.
Ross, A. H. et al., *Nature*, 294, 654–656, (1981).
Schulman, M. et al., *Nature*, 276, 269–270, (1978).
Stanley, E. R. et al., *J. Imm. Methods*, 42, 253–284, (1981).
Walter, G. et al. *P.N.A.S. (U.S.A.)*, 77, 5195–5200, (1980).
Walter, G. et al., *P.N.A.S. (U.S.A.)*, 78, 4882–4886, (1981).
Weir (ed.), *Handbook of Experimental Immunology*, vol. 1, (Blackwell Scientific Publications, 1978), pp. 19.10–19.14.
Wong, T. W. et al., *P.N.A.S. (U.S.A.)*, 78, 7412–7416, (1981).
Wu, M. et al., *J. Biol. Chem.*, 254, 6226–6228, (1979).
Wu, M. et al., *J. Clin. Invest.*, 65, 772–775, (1980).

*Primary Examiner*—Benjamin R. Padgett
*Assistant Examiner*—M. Moskowitz
*Attorney, Agent, or Firm*—Marshall, O'Toole, Gerstein, Murray & Bicknell

[57] ABSTRACT

Murine-derived hybridoma tumor cell lines and monoclonal anti-Colony Stimulating Factor Subclass Number 1 antibody substances produced by these cell lines. Use of said monoclonal antibody substances, alone or in combination, in immunological procedures for isolation of natural Colony Stimulating Factor Subclass Number 1 and for quantitative detection of colony Stimulating Factor Subclass Number 1 in fluid samples.

21 Claims, No Drawings

HYBRIDOMA TUMOR CELL LINES AND THEIR MONOCLONAL ANTIBODIES TO HUMAN COLONY STIMULATING FACTOR SUBCLASS NUMBER 1

BACKGROUND OF THE INVENTION

The present invention relates generally to materials and methods for use in immunological procedures for isolation and quantitative detection of colony stimulating factor, commonly known as "CSF", from biological fluids. More specifically, the invention relates to two monoclonal anti-CSF-1 antibodies, produced by two novel hybridoma cell lines (A.T.C.C. HB8207 and A.T.C.C. HB8208) and to uses of these antibodies in diagnostic assays of CSF-1 content on human and animal fluids and in procedures for isolating CSF-1 in quantity.

The cells of the immune system that respond to the presence of antigenic substances in the body originate from hematopoietic tissue, the bone marrow. Approximately one-half of the tissue in bone marrow is dedicated to hematopoiesis or blood cell formation. The development of blood cells arises from primitive undifferentiated stem cells and diverges into several distinct lines which include, among others, cells of the granulocytic and monocytic series (i.e., macrophages, monocytes, granulocytes).

Colony stimulating factors ("CSFs") are glycoprotein hemopoietic cell growth factors which, in semisolid culture media, stimulate the growth and differentiation of hemopoietic precursor cells into colonies of granulocytes and/or macrophages. At least four separable subclasses of CSF have been identified, each exhibiting different physical properties and target cell specificities. The subclasses have been described by reference to the types of mature cells they stimulate production of in culture. One subclass stimulates macrophage production exclusively; a second stimulates neutrophilic granulocyte and macrophage production; a third stimulates neutrophilic granulocyte production; and a fourth stimulates eosinophilic granulocyte production.

CSF-1 is the most clearly delineated subclass of CSF. It stimulates the proliferation of cells of the mononuclear phagocytic series, (i.e., undifferentiated cells, blood mononuclear cells and macrophages) only. In the absence of CSF-1 undifferentiated mononuclear phagocytic cells rapidly become unresponsive or die, while macrophages survive, but in a non-proliferating state. In the presence of CSF-1, responsive cells have a finite proliferative capacity that decreases as the cells mature. Both cell types elevate their secretion of plasminogen activation in response to CSF-1. CSF-1 is the only subclass to be unambiguously defined by subclass specific radioimmunoassays and radioreceptor assays. Specific cell surface receptors which mediate the biological effects of this subclass occur exclusively on mononuclear phagocytic cells. CSF-1 has been purified from several murine sources, human lung tissue, human urine and human pancreatic tumor cells. It is a sialic acid glycoprotein with a molecular weight of 40,000–70,000.

Information concerning the structure-function relationships of CSF-1 has been limited due to difficulties involved in obtaining even microgram amounts of the material in purified form. CSF-1 comprises only about 0.1% of the total protein of the most suitable starting materials, so that its purification requires large starting volumes. Additionally, many primary tissue sources because of contamination with serum, contain too large a quantity of heterogenous glycoproteins from which separation of CSF-1 is difficult. A presently more desirable source of CSF-1 is a human pancreatic carcinoma cell line, MIA-Pa-Ca-2 (A.T.C.C. CRL 1420), which reported to secrete relatively large amounts of CSF-1 into serum-free conditioned medium. Wu, et al., $J.Cl$ $n.Invest.$, 65, 772–775 (1980). A method for purification of CSF-1 to apparent homogeneity from the medium of the MIA-Pa-Ca-2 cells is described in Wu, et al., $J.Biol.$ $Chem.$, 254, 6226–6228 (1979). Other reports of studies on the structure, function and assay of CSF-1 are found in the following: Stanley, et al., $J.Imm.Methods$, 4, 253–284 (1981); Das, et al., $Blood$, 58, 630–641 (1981); Das, et al., $J.Cellular Physiol.$, 104, 359–366 (1980); and Das, et al., $J.Biol.Chem.$, 257, 13679–13684 (1982).

Pure human CSF-1 in quantity would provide a desirable reagent for biological studies on the mechanism of hormone action in the immune system and could be specifically applied in immunoassays, such as radioimmunoassays ("RIAs"), enzyme linked immunosorbent assays ("ELISAs"), and the like, for quantitative detection of CSF-1 in biological fluids such as blood, serum and urine. Highly purified CSF-1 may also have therapeutic potential in the treatment of cancer patients displaying decreased granulocyte production and/or reduced circulating peripheral granulocyte count resulting from chemotherapy. Inhibition of bone marrow precursor cells due to radiation exposure or chemotherapy puts the patient at a risk of infection by disabling the circulating cells of the immune system and, in fact, decrease in blood granulocytes is often the principal factor limiting the amount of chemotherapy or radiation therapy prescribed. Administration of pure CSF-1 thus has the potential for increasing production of cells of the immune system, and consequently increasing the therapeutic to toxic ratio of anti-cancer drugs.

Of interest to the background of the invention is current research focused on hybridoma techniques for producing tumor cell lines which will manufacture highly specific monoclonal antibody to a selected antigenic substance. Techniques used for the production of monoclonal antibodies are generally well known in the art. A typical description of these procedures may be found in Oi, V. T. and L. A. Herzenberg, "Immuno globulin Producing Hybrid", Mishell, B. B. and S. M. Shiigi (eds.), $Selected\ Methods\ in\ Cellular\ Immunolog$ San Francisco: W. H. Freeman Publishing, 197 Briefly summarized, lymphocytes removed from the spleen of an animal previously injected with the antigen of interest are induced to fuse with myeloma cells in the presence of polyethylene glycol. Thousands of "hybrid" myeloma cells are produced from the fusion. The supernatant from growth of each "hybridoma" cell culture is tested for the presence of the desired antibody activity. When such activity is found in the supernatant of one cell culture, it is cloned by limiting dilutions, and the clones produced are individually assayed for supernatant activity.

Due to the highly specific nature of their immunological properties, monoclonal antibodies developed according to hybridoma techniques have been proposed for use as diagnostic reagents, therapeutic agents, and agents for affinity purification of specifically cross-reactive antigenic proteins from crude sources. See, e.g Chisholm, *High Technology*, 3, pp. 57–63 (1983) and U.S. Pat. Nos. 4,172,124 and 4,196,265.

While there exists a substantial need for specific monoclonal anti-CSF-1 antibodies for use in obtaining useful quantities of pure CSF-1 to advance on-going research concerning hematopoiesis and for potential use in treatment of immune cell deficiencies in patients undergoing anti-cancer treatments, there have been no reports of the successful use of hybridoma techniques in obtaining a monoclonal antibody to CSF-1.

BRIEF SUMMARY

The present invention provides a new mouse-mouse, hybridoma cell line, A.T.C.C. HB8207, which provides as a component of the supernatant of its growth a highly specific monoclonal anti-CSF-1 antibody. The invention also provides a new mouse-mouse hybridoma cell line A.T.C.C. HB8208 which produces as a component of the supernatant of its growth a monoclonal antibody specifically immunoreactive with CSF-1. Tumor cells lines A.T.C.C. HB8207 and A.T.C.C. HB8208 are on deposit at the American Type Culture Collection, 12301 Parklawn Drive, Rockville, Md. 20852, a recognized public depository for cell cultures and microorganisms.

As another aspect of the present invention, there is provided a monoclonal antibody specifically immunoreactive with CSF-1 and with a low molecular weight polypeptide substantially duplicative of a portion of the amino acid sequence of CSF-1. A presently preferred amino acid sequence for such an immunoreactive polypeptide "fragment" comprises part or all of the following putative amino acid sequence of CSF-1 (commencing with the amino terminal:

RNH-Leu-Pro-Pro-Asp-Val-Glu-Phe-Asp-Arg-Pro-Phe-Leu-Arg-Ile-COR', wherein R and R' are the same or different amino acid residues or R may be hydrogen or R' may be a hydroxyl group. A most preferred sequence would specifically comprise the hydrophilic series of amino acids:

RNH-Asp-Val-Glu-Phe-Asp-COR', wherein R and R' are the same or different amino acid residues or R may be hydrogen or R' may be a hydroxyl group.

According to the practice of the present invention, a tumor cell line is produced using a standard immunological technique, as described in Oi and Herzenberg, "Immunoglobulin Producing Hybrid", supra. Spleen cells from mice, hyperimmunized with CSF-1 isolated from a human pancreatic cell line, are fused with a mouse myeloma cell line in the presence of polyethylene glycol. The supernatant from growth of each "hybridoma" cell culture is tested for the presence of the desired antibody activity. When such activity is found in the supernatant of one cell culture, it is cloned by limiting dilutions and the clones produced are individually assayed for supernatant activity. A selected hybridoma cell cloned to propagate a cell line can produce an antibody in its growth supernatant which has highly specific anti-CSF-1 antibody action.

According to the invention, each of the two new monoclonal antibodies produced by hybridomas A.T.C.C. HB8207 and A.T.C.C. HB8208 or the anti-polypeptide antibody may be employed in immunological procedures for affinity purification and isolation of biologically active CSF-1 from a biological fluid. In such a procedure, a selected antibody would be immobilized (e.g., on a column) and the biological fluid would be contacted with the immobilized antibody. CSF-1 would bind to the antibody and would thereafter be eluted from the immobilized antibody in a highly purified form. Antibodies of the invention may also be employed separately or jointly in immunological procedures for the quantitative detection of CSF-1 in a biological fluid, particularly a human fluid, including whole blood, serum and urine.

The present invention further provides an immunological assay for quantitative detection of CSF-1 in a biological fluid sample involving the following general steps: (1) contacting the fluid with a first, immobilized, antibody which reacts with a first antigenic determinant of CSF-1 in the sample to form an immunological complex; (2) contacting the complex so formed with a second antibody which reacts with an antigenic determinant of CSF-1 other than the first antigenic determinant; and (3) quantifying the amount of the second antibody bound to the immunological complex. The first or second antibody in this type assay may be either the monoclonal antibody produced by tumor cell line A.T.C.C. HB8207 or the monoclonal antibody produced by tumor cell line A.T.C.C. HB8208 or the above-noted anti-polypeptide antibody. Polyvalent antibodies against CSF-1 may also be useful in such procedures.

Other aspects and advantages of the present invention will become apparent upon consideration of the following detailed description.

DETAILED DESCRIPTION

The following examples illustrate practice of the invention in the production of hybridoma cell lines A.T.C.C. HB8207 and A.T.C.C. HB8208, the isolation of monoclonal antibodies to CSF-1, and the characterization, amplification and properties of the monoclonal antibodies which each possess immunological attractions for an antigenic determinant of CSF-1.

More particularly, Examples 1 through 3 are directed to stimulation of a mouse toward production of polyclonal mouse serum antibodies to CSF-1; fusion of mouse spleen cells with mouse myeloma cells; and the screening, cloning and growth of hybridoma cells and isolation of monoclonal antibody therefrom, anti-CSF-1 antibody. Examples 4 and 5 relate to the amplification of monoclonal antibody yields by the ascites method; and the determination of properties of those monoclonal antibodies.

EXAMPLE 1

Production of Polyclonal Serum

In the procedure for production of hybridoma cell lines, A.T.C.C. HB8207 and A.T.C.C. HB8208, BALB/C mice (Simonsen Laboratories, Gilroy, Calif.) are hyperimmunized to the glycoprotein CSF-1 by inoculation with 10% pure human CSF-1 ("crude" CSF-1). The CSF-1 used for the inoculations was isolated from an established human pancreatic carcinoma cell line, MIA-Pa-Ca-2, A.T.C.C. CRL 1420. The procedures for purification of CSF-1 from MIA-Pa-Ca-2 cells cultured in serumfree conditioned medium to "purified" CSF-1 involve preparative isoelectrofocusing, gel filtration chromatography and microgel electrophoresis, as described in Wu, et al., *J.Biol.Chem.*, 254, 6226–6228 (1979), and Wu, et al., *J.Clin. Invest.*, 65, 772–775 (1980).

10% pure human CSF-1 ("crude" CSF-1) was obtained from the CSF-1 from the MIA-Pa-Ca-2 cell culture by only the isoelectrofocusing and gel filtration methods described above. The final microgel electrophoresis step was omitted for obtaining "crude" CFS-1. Activity of the CSF-1 isolate was verified by bioassay of activity in stimulating cell colony formation. The first inoculation was subcutaneous and contained 30 micrograms of "crude" CSF-1 plus Freunds Complete Adjuvant (Difco Laboratories). Second and third inoculations, given intraperitoneally 8 and 17 days, respectively, after the subcutaneous injection, also contained 30 micrograms "crude" CSF-1. Three days prior to cell fusion, the mice were inoculated with a final intraperitoneal injection containing 3 micrograms "purified" CSF-1.

After the three injections, serum from several mice was assayed by a radioimmunoprecipitation assay and polyacrylamide gel electrophoresis for the presence of specific polyclonal serum antibodies to "purified" CSF-1.

A. Radioimmunoprecipitation

"Purified" CSF-1, purified from MIA-Pa-Ca-2 cultured cells as described above, is iodinated with radiolabelled $Na^{125}I$ to provide a radioactivity level of approximately $10^5$ to $10^8$ counts per minute per microgram of CSF-1. Serum from several mice inoculated with CSF-1 is reacted with the labelled CSF-1 in a radioimmunoprecipitation procedure [See, Kessler, *Methods in Enzymology*, 73, 442–458 (1981)] to give a CSF-1 antibody titer of greater than 1:100.

Results of the assay show 50% precipitation of labelled CSF-1 (approximately 0.165 ng input $^{125}I$-CSF-1) occurs at a serum dilution of approximately $4 \times 10^{-3}$. Serum diluted to $10^{-1}$ causes 100% precipitation of labelled CSF-1 antigen in solution and a serum dilution of $10^{-4}$ precipitated only 3% of antigen. This assay demonstrates that polyclonal antibody to CSF-1 is produced in mouse serum following the above three inoculations.

B. SDS-PAGE of $^{125}$-CSF-1

The immune complexes of CSF-1 and polyclonal antibody which precipitated out in the above RIP assay were disassociated. Disassociated immunoprecipitate and pure $^{125}I$-CSF-1 were autoradiographed on sodium dodecyl sulfate polyacrylamide gel (SDS-PAGE). Results of this electrophoretic separation indicate that both the disassociated immune complex and the labelled $^{125}I$-CSF-1 banded out on the gel at similar molecular weights.

EXAMPLE 2

Cell Fusion

Following verification that the inoculated mice were producing polyclonal antibodies to CSF-1 in serum, spleens of the immunized BALB/C mice, which contain a small number of CSF-1 antibody-producing lymphocytes, are disrupted to single cells. In the presence of the fusogen polyethylene glycol, immune donor spleen cells are fused with a parental BALB/C myeloma cell line, SP2/0-[HPRT−] [Schulman, et al., *Nature*, 276, 269 (1978)] to produce a variety of hybrids. Briefly described, cell membranes fuse and initially surround a common cytoplasm with two or more nuclei. Several days after that event, the nuclei fuse and become capable of synchronous mitosis. As these fused cells divide, a variable number of chromosomes of both fused partners are lost until the hybrid cell lines stabilize.

Fused cells are plated into five multiple 96-well plate (480 total wells) at $10^5$ to $10^6$ cells per well. Selection o SP2/0:spleen cell hybrids from the fusion which also produces SP2/0:SP2/0 and spleen:spleen cell hybrids i accomplished by culturing the fusion mixture in hypox anthineaminopterin-thymidine (HAT) medium for tw weeks. HAT medium prevents SP2/0:SP2/0 hybrid from growing. The spleen:spleen cell hybrids generall die after two weeks in culture. Thus the HAT mediun allows growth of only the SP2/0:spleen hybrid cells.

After 10 days, all 480 wells contain multiple, viabl cell colonies. Thereafter the individual cell colonies ar screened for the presence of immunoglobulins an CSF-1 specific antibodies.

EXAMPLE 3

Screening, Cloning and Characterization of Monoclonal Antibody

An enzyme-linked immunosorbent assay was per formed for the first screen of the 480 wells for the pres ence of immunoglobulin. [See, Engvall and Perlman *J.Immunology*, 109, 129 (1972)]. Additionally, a radi oimmunoprecipitation assay as in Example 1 was per formed to reveal CSF specific antibodies in the well The results of these two screening assays showed that of the 480 initial wells were positive for both immunc globulin and anti-CSF-1 antibody.

Cells from each of the five initially screened colonie were further subdivided into new 96-well plates (90 wells), and allowed to grow. These wells were agai screened by ELISA and RIP for the presence of bot immunoglobulin and anti-CSF-1 antibody. Seventee wells revealed positive results.

To isolate a single cell producing anti-CSF-1 ant body, several cells from each of the seventeen well were diluted into new 96-well plates at a calculate density of 1 cell per 4 wells. The low density assure that a high proportion of colonies will derive from single cell. Thereafter culture fluids from all wells wer assayed by ELISA and RIP in procedures describe above. The results of this cloning procedure produce five strongly positive single-cell colonies producin antibody to CSF-1 and having satisfactory cell growt rate and density, which were selected for use as CSF monoclonal antibodies.

Based on immunological properties such as describe infra, and on preliminary SDS-PAGE analysis of ant body light and heavy chain molecular weights, it wa determined that four of the five cell lines were likely t have identical genetic lineage and be directed to th same antigenic determinant of CSF-1. Of these fou representative line (A3) was selected for deposit alon with the apparently genetically and antigenically di tinct fifth (F18). A.T.C.C. HB8207 (A3) and A.T.C.C HB8208 (F18) were further selected for characteriz tion and antibody production by the following tech niques:

A. A radial immunodiffusion assay [Weir (ed.), *Hanc book of Experimental Immunology*, Vol. 1, (Blackwe Scientific Publications, 1978), pp. 19.10–19.14] and a ELISA (Engvall and Perlman, supra) are performed o culture fluids of each clone to characterize each clon product by immunoglobulin subclass. Each clone prc duces Immunoglobulin subclass IgG1.

B. To assess the ability of the clone culture fluids to precipitate labelled $^{125}$I-CSF-1, a radioimmunoprecipitation assay was performed in comparison with immune mouse serum. The maximum immunoprecipitability by the monoclonal antibodies produced by A.T.C.C. HB8207 and A.T.C.C. HB8208 (A3 and F18, respectively) is in the range of 30–35%. The maximum immunoprecipitability of $^{125}$I-CSF-1 by immune serum is approximately 45%. Due to the presence in serum of polyclonal antibodies directed to a number of antigenic determinants on the CSF-1 antigen, the immune serum precipitates a greater amount of the antigen than do the specific monoclonal antibodies, which by their nature are directed to a specific antigenic site.

To isolate maximum antibody producers, F18 and A3 were continuously subcultured to avoid deleterious effects of aging. A desirable medium for growth of hybridoma cells is HB101 (Hanna Biologicals) supplemented with 1% fetal calf serum (Tissue Culture Biologicals); when cells are in condition for harvesting culture fluid, the medium is preferably changed to HB101 and 1% fetal calf serum from which gamma-globulin has been removed.

Monoclonal antibodies may be isolated from culture fluids by AMICON filtration concentration (Amicon), followed by precipitation with ammonium sulfate. Alternatively, the concentrated culture fluids may be adsorbed to Protein A-Sepharose columns (Pharmacia Corp.) [Goding, *J.Imm.Methods*, 39, 2850308 (1980)]. In these columns, the Protein A attaches to the Fc portion of the antibody immunoglobulin, allowing other contaminants in the culture fluid to elute out of association with the antibody. Although column capacity for mouse IgG1 is low, nonethless, the antibody achieves considerable purification by this method.

EXAMPLE 4

Amplification of Antibody Yields by Ascites Method

To obtain a more concentrated antibody than that produced in tissue culture, the monoclonal antibodies of the present invention are amplified by the ascites method generally described in Kenneth, et al., (eds.), *Monoclonal Antibodies, Hybridomas: A New Dimension in Biological Analysis*, p. 403, New York: Plenum Press (1981). According to this procedure, $3 \times 10^6$ to $3 \times 10^7$ hybridoma cells of each deposited cell line were injected into the peritoneal cavities of BALB/C mice, previously treated with 0.25 ml Pristane (Aldrich Chemical Co.). Pristane treatment permits growth of tumor cells in an ascitic form within the peritoneal cavity. Once the ascitic tumor cells grow, the mice are sacrificed and the ascitic fluid containing the monoclonal antibody is harvested from the cells by centrifugation. The monoclonal antibody in the ascites fluid is then assayed for antibody titer. This procedure produces a smaller volume of monoclonal antibody which, as described infra, has a higher titer than antibody produced in tissue culture. Ascites fluid antibodies can be further purified from ascites fluid albumin by 40% ammonium sulfate precipitation and gel filtration.

EXAMPLE 5

Activity

Assays were performed on the ascites fluid monoclonal antibodies and tissue culture monoclonal antibodies from hybridoma cell lines A.T.C.C. HB8207 and A.T.C.C. HB8208 to determine the extent of their immunoreactivity with CSF-1.

A. Radioimmunoprecipitation

Radioimmunoprecipitation assays were performed to ascertain the ability of each monoclonal antibody to precipitate radiolabelled $^{125}$I-CSF-1 from solution. The assays were performed using culture fluid and ascites fluid.

The results of the assays revealed that the dilutions of culture fluid necessary to give a 50% maximum precipitation of a fixed quantity of $^{125}$I-CSF-1 for both A.T.C.C. HB8207 and A.T.C.C. HB8208 were between 1:2 and 1:10. The dilutions of ascites fluid of A.T.C.C. HB8207 required to give a 50% maximum precipitation of $^{125}$I-CSF-1 was between $1:10^4$ and $1:10^5$, while the dilutions of ascites fluid of A.T.C.C. HB8208 required to give a 50% maximum precipitation of $^{125}$I-CSF-1 was between $1:10^3$ and $1:10^4$. These results indicate that the monoclonal antibodies are indeed produced in higher titers in ascites fluid. For antibody produced by A.T.C.C. HB8208, titers for both tissue culture and ascites fluid-produced antibody was generally about 50% that of A.T.C.C. HB8207.

B. SDS-PAGE

Disassociated monoclonal antibody immunoprecipitates with $^{125}$I-CSF-1 were electrophoresed on sodium dodecyl sulfate polyacrylamide gel with disassociated immune serum immunoprecipitates and with $^{125}$I-CSF-1. All immunoprecipitates, including those of the ascites fluid monoclonals and culture fluid monoclonals, gave single bands at the appropriate molecular weight for CSF-1, approximately 52,000.

C. Competition Radioimmunoassays

Competition radioimmunoassays were performed in which unlabelled CSF-1 competed with $^{125}$I-CSF-1 for binding with the monoclonal antibodies of A.T.C.C. HB8207 and A.T.C.C. HB8208 and polyclonal (polyvalent) serum of Example 1.

In these radioimmunoassays the quantity of $^{125}$I-CSF-1 employed was approximately $1.2 \times 10^5$ counts per minute (about 0.3 nanograms or $6 \times 10^{-3}$ picomoles). The antibody input for each assay was the amount of antibody capable of binding 25% of maximum precipitable $^{125}$I-CSF-1 cpm.

The results indicated that 16-fold more unlabelled CSF-1 (by weight) than labelled $^{125}$I-CSF-1 successfully competed out 42–61% of the labelled $^{125}$I-CSF-1. More specifically, the percent inhibition of $^{125}$I-CSF-1 immunoprecipitation in the presence of a 16-fold greater amount of CSF-1 is illustrated in the following table:

TABLE I

| Antibody Source | % Inhibition |
| --- | --- |
| A.T.C.C. HB8207: culture fluid (A3) | 46% |
| ascites fluid | 48% |
| A.T.C.C. HB8208: culture fluid (F18) | 45% |
| ascites fluid | 42% |
| Polyvalent immune serum | 61% |

The data in Table I was consistent and reproducible at higher concentrations of CSF-1. However, at lower concentrations of CSF-1 the percent inhibition figures varied. For example, at a three-fold concentration of CSF-1 to $^{125}$I-CSF-1, A.T.C.C. HB8207 culture fluid and ascites fluid antibody inhibited 21–33% of radiolabelled binding, while A.T.C.C. HB8208 culture fluid antibody produced inhibition of 20% and ascites fluid antibody produced inhibition of less than 5%.

EXAMPLE 6

Development of Monoclonal Antibody Reactive with CSF-1 and a Polypeptide

In the recent past there have been numerous reports of immunological activity for synthetic polypeptides which substantially duplicate amino acid sequences extant in naturally-occurring proteins, glycoproteins and nucleoproteins. More specifically, relatively low molecular weight polypeptides have been shown to participate in immune reactions which are similar in duration and extent to the immune reactions of physiologically significant proteins such as viral antigens, polypeptide hormones and the like. Included among the immune reactions of such polypeptides is the provocation of the formation of specific antibodies in immunologically active animals. See, e.g., Lerner, et al., *Cell*, 23, 309–310 (1981); Ross, et al., *Nature*, 294, 654–656 (1981); Walter, et al., *P.N.A.S. (USA)*, 77, 5197–5200 (1980); Lerner, et al., *P.N.A.S. (USA)*, 78, 3403–3407 (1981); Walter, et al., *P.N.A.S. (USA)*, 78, 4882–4886 (1981); Wong, et al., *P.N.A.S. (USA)*, 78, 7412–7416 (1981); Green, et al., *Cell*, 28, 477–487 (1982); Nigg, et al., *P.N.A.S. (USA)*, 79, 5322–5326 (1982); Baron, et al., *Cell*, 28, 395–404 (1982); Dreesman, et al., *Nature*, 295, 158–160 (1982); and Lerner, *Scientific American*, 248, No. 2, 66–74 (1983).

Preliminary results of amino acid sequencing of CSF-1 by high pressure liquid chromatography has revealed the following amino acid sequence, commencing at the amino terminal:

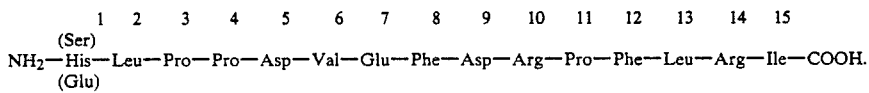

As indicated in the above representation of the preliminary sequence, doubt exists as to the identity of the initial amino acid residue; it may be either histidine, serine or glutamic acid. Analysis of the above sequence by the method of Hopp, et al., *P.N.A.S. (USA)*, 78, 3824 (1981) reveals that the sequence of amino acids spanning residues 5 through 9 (Asp-Val-Glu-Phe-Asp) is significantly hydrophilic and hence likely to be antigenic. A synthetic polypeptide whose sequence of amino acids substantially duplicates that set out above should therefore provide an immunologically active material capable of provoking formation of a highly specific antibody which will be immunologically reactive with both the polypeptide and naturally occurring CSF-1.

Consistent with the above, a synthetic polypeptide duplicating the sequence of amino acids of residues 2 through 14 is to be prepared and is expected to be successfully employed in immunization, cell fusion and cloning procedures as set out in Examples 1, 2 and 3 to provide a novel hybridoma cell line. The polypeptide may be employed as an immunogen directly or affixed (by a disulfide bond to an additional carboxy-terminal cystein residue) to a suitable "carrier" protein such as keyhole limpet hemocyanin (KLH). This cell line would be characterized by the capacity to produce monoclonal antibodies which are immunologically reactive with both CSF-1 and a synthetic polypeptide whose amino acid sequence is substantially duplicative of that of human CSF-1. Additional suitable polypeptides which could also be employed may include one of the three alternate amino terminal residues, serine, histidine or glutamic acid.

EXAMPLE 7

Isolation of CSF-1

Through its provision of highly specific and highly reactive anti-CFS-1 monoclonal antibodies, the present invention makes possible for the first time the isolation of CSF-1 from biological fluids such as blood, serum and urine by affinity purification procedures well known in the art. Briefly put, preferred isolation procedures would involve immobilizing an antibody of the invention on a solid support (e.g., a chromatographic column), contacting the CSF-1 containing fluid with the immobilized antibody and thereafter eluting purified CSF-1 from immune complex association with the antibody.

EXAMPLE 8

Quantitative Detection of CSF-1

Through its provision of highly specific anti-CSF-monoclonal antibodies, the present invention also make possible novel assays for quantitative detection of CSF-1 in a biological fluid sample which employ more than one antibody. Such assays would include the step of:

(1) contacting the fluid with a first, immobilized antibody which reacts with a first antigenic determinant of CSF-1 in the fluid to form an immunological complex of CSF-1 and the first antibody;

(2) contacting the complex formed in step (1) with second antibody which reacts with an antigenic determinant of CSF-1 other than the first antigenic determinant, to form an immunological complex of CSF-1 and the second antibody; and (3) quantifying the amount of the second antibody bound to the immunological complex formed in step (2)

Such assay procedures would preferably include two of the above-described monoclonal antibodies, but may also be developed using one of the monoclonal antibodies and a polyvalent, serum-derived antibody to CSF- Numerous modifications and variation in practice of the invention are expected to occur to those skilled in the art upon consideration of the foregoing description of preferred embodiments thereof. Consequently, only such limitations should be placed upon the scope of the invention as appear in the appended claims.

What is claimed is:

1. A murine-derived hybridoma cell line capable of producing in the medium of its growth a monoclonal antibody capable of specifically binding with Colony Stimulating Factor Subclass Number 1 in an antigen/antibody complex.

2. A hybridoma cell line according to claim 1 which is ATCC No. HB8207.

3. A hybridoma cell line according to claim 1 which is ATCC No. HB8208.

4. A monoclonal antibody produced by a hybridoma cell line according to claim 1.

5. A monoclonal antibody produced by hybridoma cell line ATCC No. HB8207 according to claim 2.

6. A monoclonal antibody produced by hybridoma cell line ATCC No. HB8208 according to claim 3.

7. In an immunological procedure for isolation of biologically active Colony Stimulating Factor Subclass Number 1 from a biological fluid on the basis of a selective immunological reaction with an antibody specific for Colony Stimulating Factor Subclass Number 1, the improvement comprising:
  employing the monoclonal antibody of claim 4 or 5 or 6 as said specific antibody.

8. The improvement of claim 7 wherein said fluid is a human fluid.

9. The improvement of claim 7 wherein said fluid is a member of the group comprising whole blood, serum and urine.

10. In an immunological procedure for the quantitative detection of Colony Stimulating Factor Subclass Number 1 in a biological fluid on the basis of a selective immunological reaction with an antibody specific for Colony Stimulating Factor Subclass Number 1, the improvement comprising:
  employing the monoclonal antibody of claim 4 or 5 or 6 as said specific antibody.

11. The improvement of claim 10 wherein said fluid is a human fluid.

12. The improvement of claim 10 wherein said fluid is a member of the group comprising whole blood, serum and urine.

13. The improvement of claim 10 wherein said immunological procedure is a radioimmunobinding assay.

14. A monoclonal antibody produced by a murine-derived hybridoma cell line according to claim 1, said antibody capable of specifically binding in an antigen-antibody complex with that portion of a polypeptide which consists essentially of an amino acid sequence comprising: NHR-Asp-Val-Glu-Phe-Asp-COR', wherein R and R' are the same or different amino acid residues or R is hydrogen or R' is a hydroxyl group.

15. The product according to claim 14 wherein the amino acid sequence of the polypeptide comprises: RNH-Leu-Pro-Pro-Asp-Val-Glu-Phe-Asp-Arg-Pro-Phe-Leu-Arg-COR', wherein R and R' are the same or different amino acid residues or R is hydrogen or R' is a hydroxyl group.

16. The product of claim 15 wherein R is selected from the group consisting of serine, histidine, and glutamic acid and R' is cystein.

17. An immunological assay for quantitative detection of Colony Stimulating Factor Subclass Number 1 in a biological fluid sample comprising the steps of:
  (1) contacting said fluid with a first, immobilized, antibody which reacts with a first antigenic determinant of Colony Stimulating Factor Subclass Number 1 in said fluid to form an immunological complex of Colony Stimulating Factor Subclass Number 1 and said first antibody;
  (2) contacting the complex formed in step (1) with a second antibody which reacts with an antigenic determinant of Colony Stimulating Factor Subclass Number 1 other than said first antigenic determinant, to form an immunological complex of Colony Stimulating Factor Subclass Number 1 and said second antibody; and
  (3) quantifying the amount of said second antibody bound to said immunological complex formed in step (2).

18. The assay according to claim 17 wherein said first antibody is a monoclonal antibody produced by a murine-derived hybridoma cell line capable of producing in the medium of its growth a monoclonal antibody capable of specifically binding with Colony Stimulating Factor Subclass Number 1 in an antigen/antibody complex and said second antibody is selected from the group consisting of a serum-derived polyvalent antibody to Colony Stimulating Factor Subclass Number 1, or a monoclonal antibody produced by hybridoma cell line ATCC No. HB8207, or a monoclonal antibody produced by hybridoma cell line ATCC No. HB8208 or a monoclonal antibody produced by a murine-derived hybridoma cell line capable of producing in the medium of its growth a monoclonal antibody capable of specifically binding with Colony Stimulating Factor Subclass Number 1 in an antigen/antibody complex, said antibody capable of specifically binding in an antigen/antibody complex with that portion of a polypeptide which consists essentially of an amino acid sequence comprising: NHR-Asp-Val-Glu-Phe-Asp-COR', wherein R and R' are the same or different amino acid residues or R is hydrogen or R' is a hydroxyl group.

19. The assay according to claim 17 wherein said first antibody is a monoclonal antibody produced by hybridoma cell line ATCC No. HB8207, and said second antibody is selected from the group consisting of a serum-derived polyvalent antibody to Colony Stimulating Factor Subclass Number 1, or a monoclonal antibody produced by a murine-derived hybridoma cell line capable of producing in the medium of its growth a monoclonal antibody capable of specifically binding with Colony Stimulating Factor Subclass Number 1 in an antigen/antibody complex, or a monoclonal antibody produced by hybridoma cell line ATCC No. HB8208, or a monoclonal antibody produced by a murine-derived hybridoma cell line capable of producing in the medium of its growth a monoclonal antibody capable of specifically binding with Colony Stimulating Factor Subclass Number 1 in an antigen/antibody complex, said antibody capable of specifically binding in an antigen/antibody complex with that portion of a polypeptide which consists essentially of an amino acid sequence comprising: NHR-Asp-Val-Glu-Phe-Asp-COR', wherein R and R' are the same or different amino acid residues or R is hydrogen or R' is a hydroxyl group.

20. The assay according to claim 17 wherein said first antibody is a monoclonal antibody produced by hybridoma cell line ATCC No. HB8208, and said second antibody is selected from the group consisting of a serum-derived polyvalent antibody to Colony Stimulating Factor Subclass Number 1, or a monoclonal antibody produced by a murine-derived hybridoma cell line capable of producing in the medium of its growth a monoclonal antibody capable of specifically binding with Colony Stimulating Factor Subclass Number 1 in an antigen/antibody complex, or a monoclonal antibody produced by hybridoma cell line ATCC No. HB8207 or a monoclonal antibody produced by a murine-derived hybridoma cell line capable of producing in the medium of its growth a monoclonal antibody capable of specifically binding with Colony Stimulating Factor Subclass Number 1 in an antigen/antibody complex, said antibody capable of specifically binding in an antigen/antibody complex with that portion of a polypeptide which consists essentially of an amino acid sequence comprising: NHR-Asp-Val-Glu-Phe-Asp- COR', wherein R and R' are the same or different amino acid residues or R is hydrogen or R' is a hydroxyl group.

21. The assay according to claim 17 wherein said first antibody is a monoclonal antibody produced by a murine-derived hybridoma cell line capable of producing in the medium of its growth a monoclonal antibody capable of specifically binding with Colony Stimulating Factor Subclass Number 1 in an antigen/antibody complex, said antibody capable of specifically binding in an antigen/antibody complex with that portion of a polypeptide which consists essentially of an amino acid sequence comprising: NHR-Asp-Val-Glu-Phe-Asp-COR', wherein R and R' are the same or different amino acid residues or R is hydrogen or R' is a hydroxyl group, and said second antibody is selected from the group consisting of a serum-derived polyvalent antibody to Colony Stimulating Factor Subclass Number 1 or a monoclonal antibody produced by a murine derived hybridoma cell line capable of producing in the medium of its growth a monoclonal antibody capable of specifically binding with Colony Stimulating Factor Subclass Number 1 in an antigen/antibody complex, or a monoclonal antibody produced by hybridoma cell line ATCC No. HB8207 or a monoclonal antibody produced by hybridoma cell line ATCC No. HB8208.

* * * * *